US00PP26705P3

(12) United States Plant Patent
Sparks

(10) Patent No.: US PP26,705 P3
(45) Date of Patent: May 10, 2016

(54) PECAN TREE NAMED 'TOM'

(50) Latin Name: *Carya illinoinensis*
Varietal Denomination: Tom

(71) Applicant: University of Georgia Research Foundation, Inc., Athens, GA (US)

(72) Inventor: Darrell Sparks, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 95 days.

(21) Appl. No.: 14/121,659

(22) Filed: Oct. 3, 2014

(65) Prior Publication Data

US 2016/0100512 P1 Apr. 7, 2016

(51) Int. Cl.
*A01H 5/02* (2006.01)

(52) U.S. Cl.
USPC ..... Plt./153

(58) Field of Classification Search
USPC ..... Plt./153
See application file for complete search history.

*Primary Examiner* — Anne Grunberg
(74) *Attorney, Agent, or Firm* — Klarquist Sparkman, LLP

(57) ABSTRACT

A pecan tree distinguished by the following unique combination of characteristics: high prolificacy, consistent production, early nut maturity, kernel size suited to confection trade, excellent color, absence of kernel speckling, excellent resistance to the scab fungus (*Fusicladosporium effusum*), and high resistance but not immunity to black aphid (*melanocallis caryaefoliae*) and leaf scorch mite (*Eotetranychus hicoriae*).

5 Drawing Sheets

Latin name of the genus and species of the plant: *Carya illinoinensis.*

Variety denomination: 'Tom'.

BACKGROUND OF THE INVENTION

The present invention relates to a new and distinct variety of pecan tree named 'Tom'. My new tree can be used in gardens or for commercial production of pecan nuts. This new tree was selected from seedlings grown from controlled pollination in Watkinsville, Ga., in 1989. The 'Tom' selection resulted from crossing 'Wichita' (unpatented) as the seed parent with 'Pawnee' (unpatented) as the pollen parent. The resulting tree was selected when growing in a cultivated area at Watkinsville, Ga.

BRIEF SUMMARY OF THE INVENTION

'Tom' is distinguished from other pecan varieties known to the inventor due to the following unique combination of characteristics: High prolificacy, consistent production, early nut maturity, a kernel size suited to the confection trade, excellent kernel color, absence of kernel speckling, and excellent resistance to the scab fungus (*Fusicladosporium effusum*), and high resistance but not immunity to black aphid (*melanocallis caryaefoliae*) and pecan leaf scorch mite (*Eotetranychus hicoriae*).

Asexual reproduction of 'Tom' by grafting (top working) onto 'Desirable' (unpatented) pecan trees in 2006 and 2011 at NILO Plantation, Albany, Ga. and experimental plantings at NILO in 2011 and 2012 and at Graham Pecan Farm, Leary, Ga. in 2009 and at Ray City, Ga. in 2011 was performed in order to evaluate these trees. Asexual reproduction of 'Tom' has shown that the forgoing characteristics come true to form, are firmly fixed, and are established and transmitted through succeeding propagations.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart, 2001. The color characteristics of this type may vary with lighting and other conditions. Therefore, color characteristics of this new variety should be determined with reference to the observations described herein, rather than from these illustrations alone.

DETAILED DESCRIPTION

Figure 1:
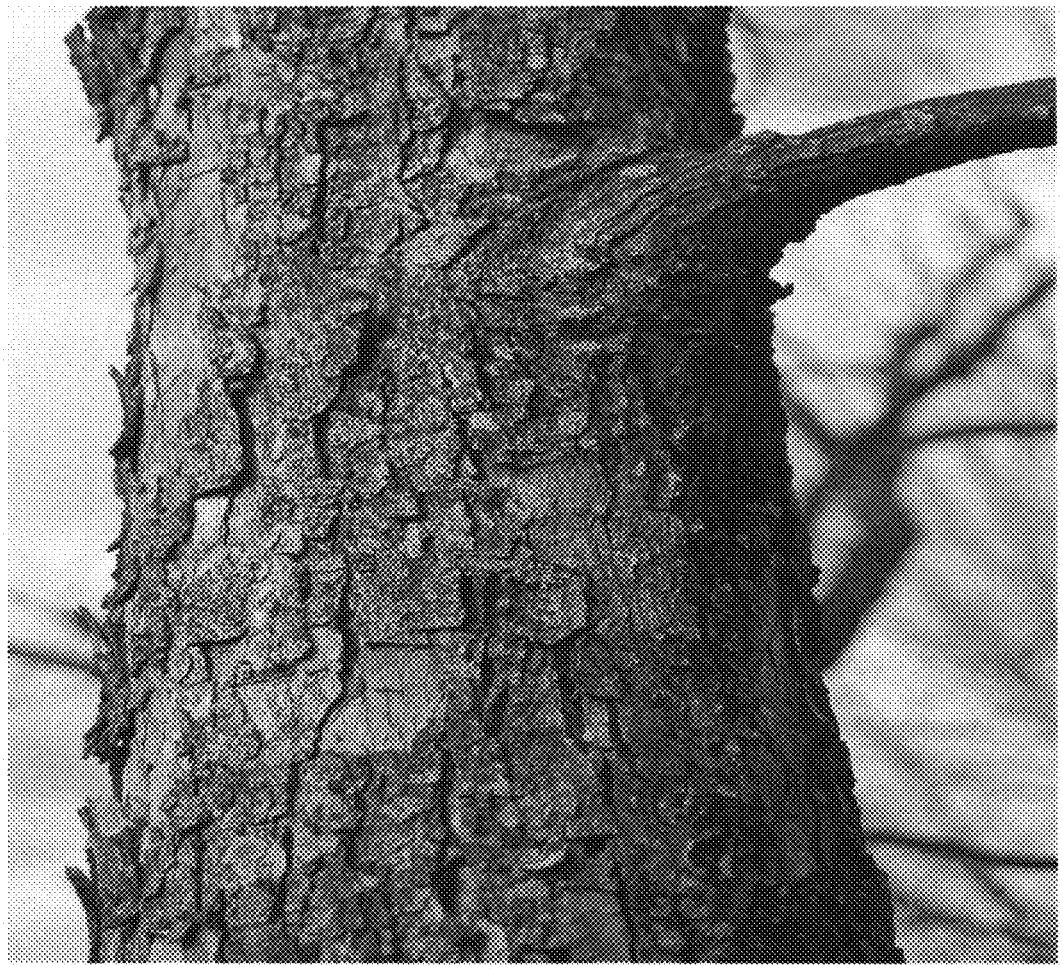
FIG. 1 is a photograph showing scaly bark of 'Tom'. Initially the bark is tight and the scaly characteristic develops with tree maturity.

Botanical: The following detailed description of 'Tom' is based on observations of the original tree growing in Watkinsville, Ga. and of asexually reproduced progeny growing in Albany, Ga. and Leary, Ga.

*Varietal name*.—'Tom'.

*Parentage*.—Seed parent: 'Wichita'. Pollen parent: 'Pawnee'.

*Tree*.—Overall shape: moderately spreading, height to width ratio is about 0.7. Vigor: Vigorous. Height: Of original tree, about 10 meters. Width: Of original tree, about 15 meters. Trunk: Of original tree (measured 0.5 m above ground level) about 0.4 m circumference. Trunk bark texture: Scaly with tree maturity. Trunk bark color: Grey (RHS 202B). Patches: Trunk has no markings. Shoot: Shoots in woody stage are Grey-brown (RHS 199A) in color, smooth in texture with Grey-brown lenticels (RHS 199D) that are elliptical shaped and about 0.8 mm long by 0.1 mm wide. There are about 151 lenticels per square cm. Branch Color: Grey-brown (RHS 201C). Internodes: Average internode length is about 0.9 cm, between the $3^{rd}$ and $4^{th}$ leaf from base of shoot. Bearing: Not precocious but prolific. Original tree fruited 11 years from seed. 'Tom' fruited the second year after grafting (top working) onto 'Desirable' trees, and has fruited consistently in subsequent years. Disease and insect resistance: High resistance to black pecan aphid [*Melanocallis caryaefoliae* (Davis)] (Table 12). High resistance to pecan leaf scorch mite [*Eotetranychus hicorire* (McGregor)] (Table 13). No scab disease [*Fusicladosporium effusum* (G. Winters) Partridge & Morgan-Jones.] has been observed on sprayed trees (Tables 14-17); but during the excessively wet 2013 growing season slight scab (lesions barely detectable) occurred on about 2% of the fruit on an unsprayed tree at Watkinsville but not on an unsprayed tree in Albany.

*Leaves*.—The mature leaf is odd pinnate compound, deciduous with leaflets having a dark green upper surface and a lighter green lower surface. Each mature leaf has from 9 to 15 leaflets. Leaflets droop from the rachis, curve inward and form a tunnel configuration. One margin of the leaflets flares upward creating a ruffed appearance (see FIG. 2). Size of mature leaf (fourth leaf from base of shoot): 30.9 cm long, 21.9 cm wide. Peduncle: Oval in cross-section, tan in color (RHS 199B). The length of the peduncle of the fourth leaf from the base is about 2.9 cm. The diameter of the peduncle of the fourth leaf from the base is about 2.0 mm. Leaflet: Size and shape: Fourth leaflet on fourth leaf from base 11.7 cm long by 2.9 cm wide. Falcate in shape. Base oblique. Margin serrate. Leaflets are convoluted which increases acropetally on the leaf and on leaves on the shoot. Texture: Smooth. Sheen: Glossy. Petiole: Sessile. Margin: Serrate. Tip shape: Acuminate and narrow. Leaflet color: Upper leaf surface: Forest green (RHS 137A). Lower leaf surface: Green (RHS 138A). Pubescence: Upper leaf surface is not pubescent. Lower surface is pubescent. The length, width and other measurements were obtained from observations of a typical leaf.

*Inflorescence*.—General: The 'Tom' pecan is monoecious, anemophilous. Dichogamy is protandrous, pollinated by 'Schley' (unpatented) and 'Elliott' (unpatented). 'Tom' will pollinate its pollinizers (see Table 2). Flowers: Pistil flowers are borne on a determinate spike, with staminate flowers borne on a determinate pendulous catkin. Two-six individual pistillate flowers per spike, borne alternately on terminally-positioned spikes. The pistillate flower is symmetrical with no stamens or petals. Pedicels: none. The staminate or catkin length is 59 mm and width is 5 mm. The staminate color is Green (RHS 144B) with gold pollen (RHS 3A). The involucre size, which includes the stigma, is 4.1 mm long by 2.0 mm wide. The flower has one pistil with an oxblood (RHS 61A) stigma. The flower has four bracts, which are green (RHS 144A), linear, lanceolate, 3.9 mm long by 1.0 mm wide and are fused at the bases, forming a copular involucre.

Figure 3:
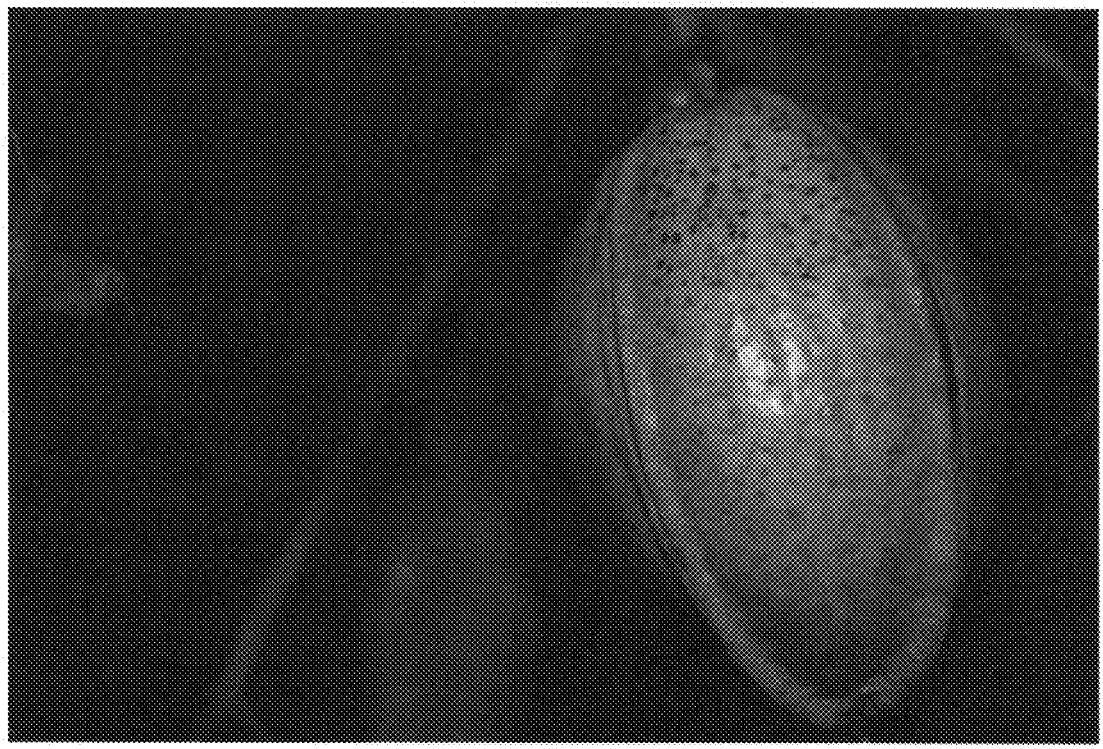
FIG. 3 is a photograph showing the characteristic stippled shuck of 'Tom'. Stippling is a distinguishing characteristic.
Figure 4:
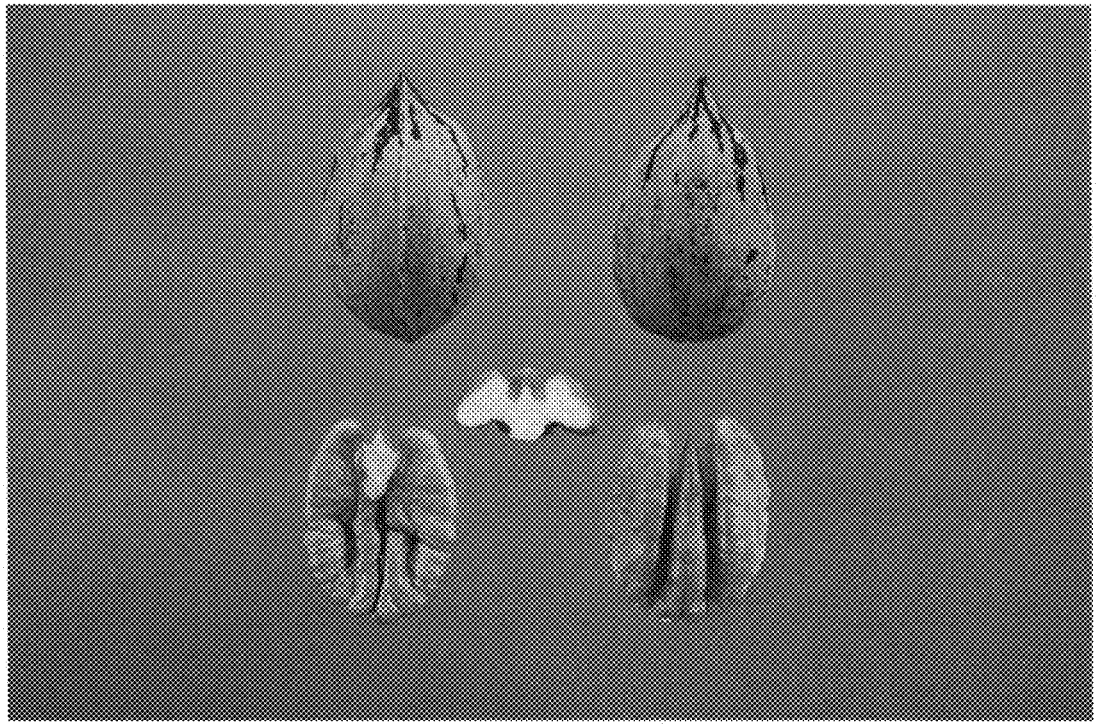
FIG. 4 is a photograph showing nut shape and kernel characteristics of 'Tom'. Nut: left to right; suture side, non-suture side. Kernel: left to right; ventral side, dorsal side. Cross section, dorsal side up.
Figure 5:
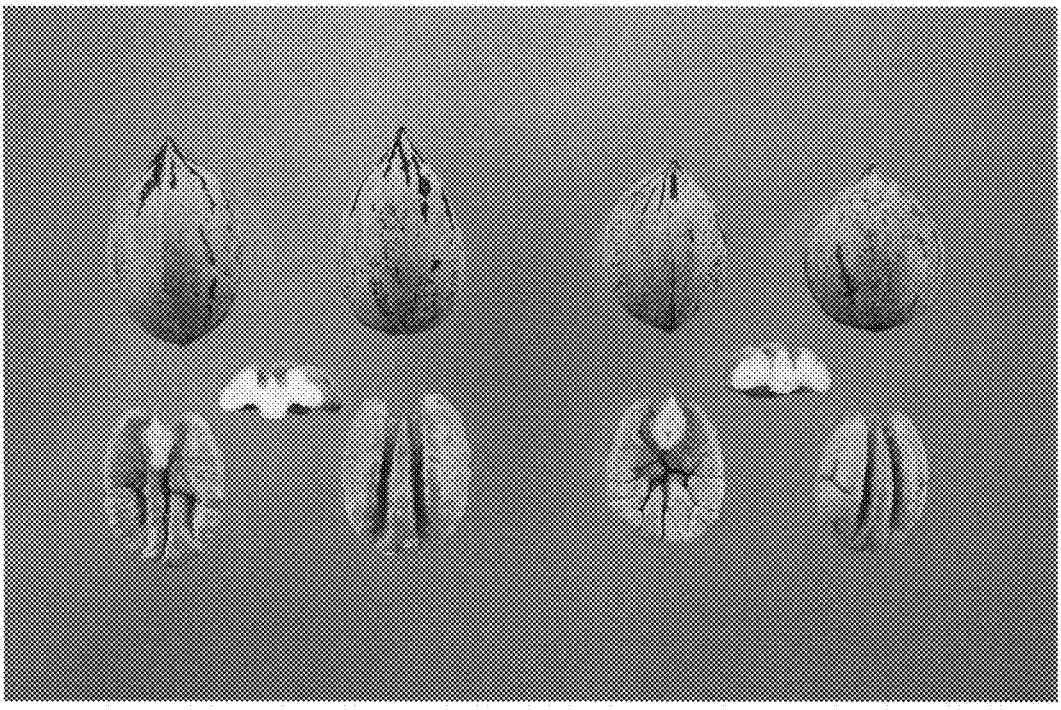
FIG. 5 is a photograph showing nut shape and kernel characteristics of 'Tom' in comparison to 'Elliott' (unpatented). Nut: left to right; 'Tom' suture side, non-suture side; 'Elliott' suture side, non-suture side. Kernel: left to right; 'Tom' ventral side, dorsal side; 'Elliott' ventral side, dorsal side. Kernel cross section: left to right 'Tom', dorsal side up; 'Elliot', dorsal side up.

*Fruit*.—Has fruited consistently thus far (see Tables 9 and 10). Mature fruit is dehiscent. Shuck: Green (RHS 144B), stippled with maturity (see FIG. 3). The shuck sutures are winged which is accentuated acropetally (see FIG. 3) and the shuck surface is not indented. Fruit split during liquid endosperm stage: Not observed to be a problem. Shuck decline: Shuck dieback during kernel formation has not been observed to be a problem.

*Nuts*.—Observations from a limited number of typical nuts from several growing seasons in Watkinsville, Ga. Size: Small (58 nuts/lb), length about 36 mm, width about 22.2 mm (width measurement taken midway along the length of the nut and across sutures); length to width ratio about 1.6. Nut flatness (ratio of width across sutures to width between sutures) is about 0.96. Form: General nut shape ovate, base round, round cross section, apex shape is slightly cuspidate, apex is grooved. Sutures: Non-elevated. Weight: 7.8 grams per nut (non-limiting soil moisture). Cluster size: About 2.8 fruits per cluster. Shell Texture: Ridged. Shell thickness: Thick, 0.84 mm. Kernel color: Good color, Greyed-orange (RHS 165B). Kernel coat: No speckling has been observed. Kernel percentage of nut: About 55 percent (non limiting soil moisture). Dorsal grooves: Wide and deep, thereby decreasing the percentage kernel in the nut. Nut maturity: September 24th and later than 'Byrd' by about 2 days. Harvestability: Suitable for machine harvest. Cracking/shelling ability: Cracks exceptionally well, percentage of kernels with intact halves is high. Typically, less than five percent of chipped or broken kernels were observed.

COMPARISONS TO OTHER VARIETIES

Figure 2:
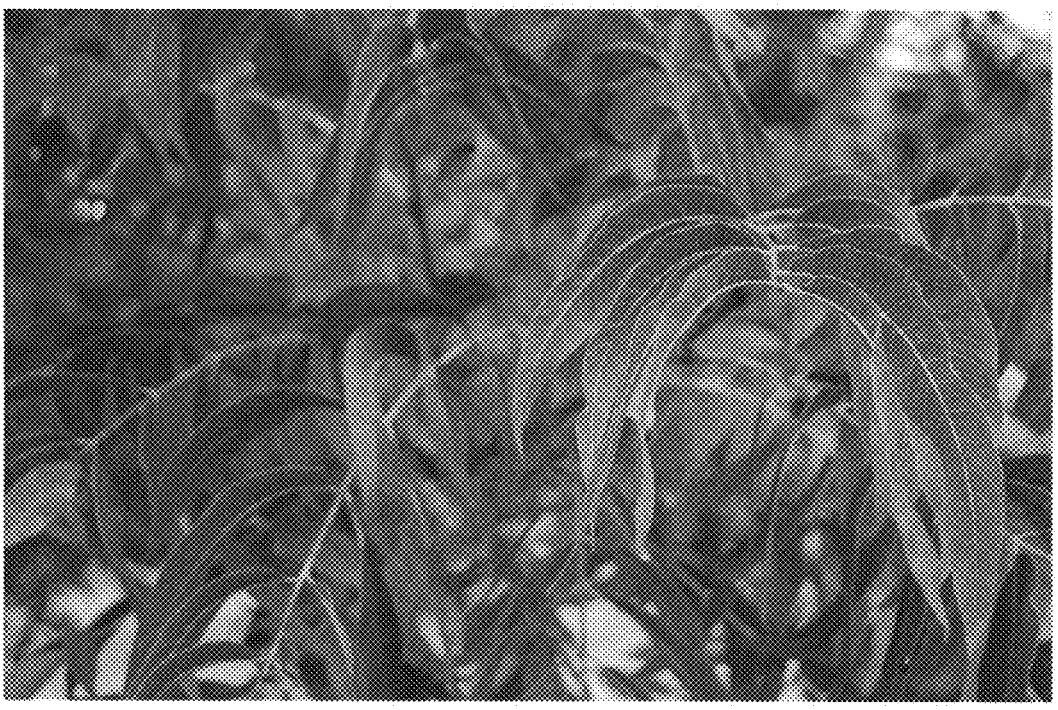
FIG. 2 is a photograph showing the leaf architecture of 'Tom'. Leaflets droop from the rachis and curve inward, forming a "tunnel" configuration. One margin of the leaflets flares upward creating a ruffed appearance. The terminal leaflet also droops and was removed (from the nearest group of leaflets shown in FIG. 2) before photographing.

The form of 'Tom' is moderately spreading and more so than either parent. The timing of bud break (Table 1) of 'Tom' is similar to 'Stuart' (unpatented) and later than 'Byrd' (U.S. Plant Pat. No. 20,867), 'Desirable, 'Huffman' (U.S. Plant Pat. No. 25,465), 'Morrill' (U.S. Plant Pat. No. 23,335), 'Cunard' (U.S. Plant Pat. No. 24,373) and 'Treadwell (U.S. Plant Pat. No. 25,740). Thus, 'Tom' is somewhat less susceptible to late-spring freezes in Georgia than most pecan varieties. The leaves of 'Tom' are forest green and darker in color than both parents and most other varieties. Leaflet orientation of 'Tom' leaves is unlike both parents, 'Huffman', 'Treadwell', 'Cunard', 'Byrd', and 'Morrill'. That is, leaflets droop from the rachis, curve inward and form a 'tunnel' configuration (FIG. 2). The stigmatic surface of 'Tom' is oxblood (RHS 61A), similar to the oxblood color of parent 'Pawnee' and in contrast to the green surface of parent 'Wichita'. In the comparison tables below, 'Cheyenne', 'Stuart', 'Schley', and 'Sumner' are unpatented varieties.

TABLE 1

Bud break date for 'Tom', 'Stuart', 'Huffman' 'Morrill, 'Byrd', 'Treadwell', and 'Cunard' pecans, Watkinsville, Georgia, 6 year average.

| Cultivar | Bud break date |
|---|---|
| 'Tom' | 4/2a |
| 'Stuart' | 3/31ab |
| 'Huffman' | 3/30b |
| 'Morrill' | 3/30b |
| 'Byrd' | 3/27c |
| 'Treadwell' | 3/27c |
| 'Cunard' | 3/26c |

Means followed by the same letter are not statistically different, P ≤ 0.05, n = 6.

TABLE 4

Comparison of kernel characteristics of 'Elliott' and 'Tom' pecans, NILO Plantation, Albany, Georgia, 2012.

| Cultivar | Kernel length (cm) | Kernel width (cm) | Kernels/lb (no.) |
|---|---|---|---|
| 'Elliott' | 2.51b | 1.88b | 268a |
| 'Tom' | 2.83a | 2.05a | 216b |

Means followed by the same letter within a column are not statistically different, P ≤ 0.05, n = 15.

TABLE 2

Approximate periods of pollen shedding and stigma receptivity for 'Tom' and selected other pecan cultivars in April, Watkinsville, Georgia.

| | April | | | | | | | | | | | | | | | | | | | | | |
|---|---|---|---|---|---|---|---|---|---|---|---|---|---|---|---|---|---|---|---|---|---|---|
| | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| Protandrous cultivars | | | | | | | | | | | | | | | | | | | | | | |
| 'Cheyenne' | | | | | | ..... | | | | | | | | | | | | | | | | |
| _ | | ___ | ___ | ___ | ___ | | | | | | | | | | | | | | | | | |
| 'Desirable' | | | | | | | | | | | | | | | ..... | | | | | | | |
| | | | ___ | ___ | ___ | | | | | | | | | | | | | | | | | |
| 'Tom' | | | | | | | | | | | | | | | ..... | ..... | ..... | | | | | |
| | | | | ___ | ___ | ___ | ___ | ___ | ___ | | | | | | | | | | | | | |
| Protogynous | | | | | | | | | | | | | | | | | | | | | | |
| 'Elliott' | | | | ..... | ..... | ..... | ..... | ..... | ..... | ..... | ..... | ..... | | | | | | | | | | |
| | | | | | | | | | | | | | | ___ | ___ | ___ | ___ | | | | | |
| 'Schley' | | | | ..... | ..... | ..... | ..... | | | | | | | | | | | | | | | |
| | | | | | | | | | | | | | | ___ | ___ | ___ | | | | | | |
| 'Stuart' | | | | | | | | | | ..... | ..... | ..... | | | | | | | | | | |
| | | | | | | | | | | | | | | | | | | | | ___ | ___ | ___ |

..... = Period of stigma receptivity.
__ = Period of pollen shedding.

TABLE 3

Comparison of nut characteristics of 'Treadwell', 'Byrd', 'Tom', 'Cunard', 'Morrill', 'Elliott', and 'Huffman' pecans, Albany, Georgia, 2009-2012.

| Cultivar | Wt./ nut (g) | Nuts/lb | Nut length (mm) | Length/ Width[z] | Nut[y] Flatness | Shell Thickness (mm) | Kernel (%) | Nut Maturity date |
|---|---|---|---|---|---|---|---|---|
| 'Treadwell' | 9.5cd | 48cd | 41.5d | 1.92b | 0.97d | 0.70bd | 62.2b | 24a |
| 'Byrd' | 8.9d | 51c | 42.4d | 1.88b | 1.04b | 0.51e | 62.3b | 24a |
| 'Tom' | 7.8e | 58b | 36.3e | 1.64c | 0.96d | 0.84a | 54.7cd | 25a |
| 'Cunard' | 11.1b | 41e | 52.2a | 2.18a | 1.03b | 0.66cd | 62.5b | 26a |
| 'Morrill' | 10.1c | 46d | 49.2b | 2.07a | 1.11a | 0.63d | 65.9a | 35b |
| 'Elliott' | 7.1f | 64a | 32.5f | 1.39d | 1.04b | 0.70bc | 52.0e | 38b |
| 'Huffman' | 12.2a | 37e | 44.7c | 1.65c | 1.03b | 0.72b | 55.5cd | 33b |

Means followed by the same letter within a column are not statistically different, P ≤ 0.05, n = 4.

[z]Length to width ratio = nut length divided by width. Width was measured midway the length of the nut and across the suture.

[y]Nut flatness = ratio of nut width across suture to width between suture. Measurement was made midway the length of the nut.

[x]Date when shuck dehiscence had occurred on 50% of the fruit, days from September 1.

TABLE 5

Susceptibility of 'Tom', 'Byrd', 'Morrill', "Huffman', 'Pawnee', 'Cunard', 'Treadwell', and 'Desirable' pecans to kernel speckling, Watkinsville, Georgia, 2000-2006, 2008, n = 8.

| Cultivar | No. of years with Kernel speckling |
|---|---|
| 'Tom' | 0 |
| 'Byrd' | 0 |
| 'Morrill' | 0 |
| 'Huffman' | 0 |
| 'Pawnee' | 4 |
| 'Cunard' | 0 |
| 'Treadwell' | 0 |
| 'Desirable' | 0 |

Pecan nuts that mature relatively early command a premium price. The price per pound normally declines as the harvest becomes later. Consequently, cultivars that exhibit early maturity at harvest are commercially important. The color of a kernel's seed coat (lighter is preferred), and the percentage kernel of the nut also affects the selling price of pecans. Nut maturity of 'Tom' is early, similar to 'Byrd', 'Cunard' and 'Treadwell', 8 days before 'Huffman' and 13 days before 'Elliott' (Table 3). 'Elliott' is believed to be the leading early, small nut cultivar planted in Georgia.

As can be seen from Tables 3 and 4, the nut size of 'Tom' nuts is slightly larger than that of 'Elliott', smaller than 'Byrd', and much smaller than 'Treadwell', 'Cunard', 'Morrill' and 'Huffman'. However, the nut length is longer in the case of 'Tom' nuts than 'Elliott' nuts and the nut shape differs. As indicated by the length to width ratio, 'Tom' nuts are more oblong than 'Elliott' nuts. In cross-section, 'Tom' nuts are near round (flatness ratio 0.96 while 'Elliott' nuts are flatter on the suture side than the non-suture side. Referring to Table 3, the shell thickness of 'Tom' is thicker than 'Treadwell', 'Byrd', 'Cunard', 'Morrill', 'Elliott' and 'Huffman'. The percentage kernel is a direct function of the shell thickness and the percentage of the shell cavity filled with the kernel. In Table 3, high percentage kernel nuts have a thin shell. The notably exception is 'Tom' which has a higher percent kernel than 'Elliott' even though the shell of 'Elliott' is much thinner. The ventral side of the kernel of 'Elliott' is concave resulting in a lower proportion percentage of the shell cavity being filled with kernel. The greater plumpness of 'Tom' makes it more suitable for the confection trade than 'Elliott'. The morphology of the dorsal grooves also affects percentage kernel. 'Morrill' has exceptional narrow and shallow grooves resulting in a very high percentage kernel. Under stress, primarily fruiting stress, when 'Pawnee' cultivar pecan trees are grown in humid southeastern United States, the kernel seed coats of nuts can develop conspicuous and unattractive dark spots. This speckling reduces the marketability of these nuts. Speckling has not been observed to be a problem of 'Tom' nuts grown in Georgia (Table 5). Kernel color is outstanding and superior to the other two early maturing varieties, 'Byrd and 'Cunard' and equal to the early 'Treadwell' and the later maturing 'Elliott'. Kernel development of 'Tom', like 'Elliott', is good during a heavy production year which contrasts with 'Pawnee' where a high percentage of the nuts can be unmarketable or of reduced value. Although not precocious (Tables 6 and 7), 'Tom' is highly prolific and is equal to the unusual prolific 'Cunard' (Table 8). Regardless, alternate or irregular bearing has not been a problem (Table 9) and consistence of production is similar to 'Huffman' and 'Morrill' (Table 10), in spite of a larger cluster size (Table 11). Unlike both parents, 'Tom' has excellent resistance to scab disease fungus which is similar to 'Huffman', better than 'Morrill', 'Cunard', 'Treadwell', 'Byrd' and much superior to 'Desirable' (Tables 14 and 15). Unlike parent 'Wichita', fruit split during the liquid endosperm stage has not been observed.

'Tom' was released as an early maturing small nut for the confection/gift package trade. Currently, 'Elliott' is the ideal nut for this trade as it produces a high percentage of intact kernels, kernel color is excellent, and the small kernel is ideal for the pecan ice cream and chocolate covered trade and its size is suited for an almond, cashew, pecan mix. 'Tom' is similar to 'Elliott' in kernel size, color, and intact halves, and scab disease resistance. It is superior to 'Elliott' in consistency of production (Tables 9 and 10), about two times more productive Tables 8 an 9), and substantial earlier nut maturity (Table 3).

TABLE 6

Precocity of 'Cunard', 'Byrd', 'Treadwell', 'Morrill', 'Desirable', 'Elliott', 'Tom', 'Huffman', and 'Stuart'.

| Variety | Years to initial fruiting[z] |
|---|---|
| 'Cunard' | 2 |
| 'Byrd' | 3 |
| 'Treadwell' | 3 |
| 'Morrill' | 4 |
| 'Desirable' | 4 |
| 'Elliott' | 5 |
| 'Tom' | 5 |
| 'Huffman' | 5 |
| 'Stuart' | 6 |

[z]Yearsfrom planting nursery trees.

TABLE 7

Nut production of young 'Tom' and 'Desirable' pecan trees, Leary, Georgia[z].

| Cultivar | Yield (lb/tree) |
|---|---|
| 'Tom' | 0.3b |
| 'Desirable' | 2.9a |

Means followed by the same letter are not statistically different, $P \leq 0.05$, n = 14.
[z]Production 4 years after top working 2 year-old trees.

TABLE 8

Production, nuts per pound, percentage kernel of trees top worked to 'Tom', 'Cunard', 'Treadwell', 'Huffman', 'Morrill', and 'Elliott' pecans, NILO Plantation, Albany, Georgia, 2009-2013.

| Cultivar | Lbs/tree | Nuts/lb. | Kernel (%) |
|---|---|---|---|
| 'Tom | 57a | 58b | 54.7cd |
| 'Cunard'[y] | 44ab | 41e | 62.5b |
| 'Treadwell'[y] | 30b | 48cd | 62.2b |
| 'Huffman' | 32b | 37e | 55.5cd |
| 'Morrill' | 35b | 46d | 65.9a |
| 'Elliott'[z] | 26b | 64a | 52.0e |

Means followed by the same letter within a column are not statistically different, $P \leq 0.05$, n = 4.
[z]Data for 'Elliott' were from non-top worked trees planted in 2002.
[y]'Cunard' and 'Treadwell' were fruit thinned as needed. About 50% of the fruit was removed. Other cultivars were not fruit thinned.

TABLE 9

Production consistency, nuts per pound, and percentage kernel of 'Tom' and 'Elliott' pecan trees, NILO Plantation, Albany, Georgia, 2009-2013. [z]

| | Lbs/tree | | Nuts/lb. | | Kernel (%) | |
|---|---|---|---|---|---|---|
| Year | 'Elliott' | 'Tom' | 'Elliott' | 'Tom' | 'Elliott' | 'Tom' |
| 2009 | 13 | 29 | 67 | 59 | 52.7 | 57.0 |
| 2010 | 43 | 34 | 62 | 62 | 50.6 | 53.0 |
| 2011 | 20 | 68 | 63 | 54 | 54.0 | 54.2 |
| 2012 | 30 | 90 | 65 | 59 | 50.9 | 53.9 |
| 2013 | 52 | 125 | 68 | 59 | 54.4 | 54.9 |
| Mean | 32 | 69 | 65 | 59 | 52.5 | 54.6 |

[z] All data are on an individual tree basis. 'Elliott' borne alternately or irregular, 'Tom' did not.

TABLE 10

Alternate bearing tendency of 'Byrd', 'Treadwell', 'Elliott', 'Huffman', 'Tom', 'Morrill', and 'Cunard' pecans, NILO Plantation, Albany, Georgia.

| Cultivar | Years to fruiting (no.) | Years until bearing alternate (no.) |
|---|---|---|
| 'Byrd' | 2 | 3 |
| 'Treadwell' | 2 | 3 |
| 'Elliott' | 2 | 4[y] |
| 'Huffman' | 2 | >7 |
| 'Tom' | 2 | >7 |
| 'Morrill' | 2 | >10 |
| 'Cunard' | 2 | 11[z] |

[y] Years after top working mature trees to the respectively cultivar, n = 3.

Top working simulates a mature tree and allows for earlier evaluation of alternate bearing, kernel development under heavy fruit load, and suitability for mechanical harvest and ease of fruit thinning.

[z] Annual production maintained by fruit thinning.

[y] Data for 'Elliott' were from non-top worked trees planted in 2002—years from initial fruiting.

TABLE 11

Fruit cluster size of 'Byrd', 'Desirable', 'Huffman', 'Tom', 'Morrill', 'Pawnee', Cunard, 'Treadwell', and 'Elliott' pecans, Watkinsville, Georgia. Data are averages of three years, 2005, 2006, and 2008.

| Cultivar | Fruits/cluster (no.)[z] |
|---|---|
| 'Byrd' | 3.1abc |
| 'Desirable' | 1.8f |
| 'Huffman' | 1.6f |
| 'Tom' | 2.8bcd |
| 'Morrill' | 2.9bcd |
| 'Pawnee' | 3.2ab |
| 'Cunard' | 3.2ab |
| 'Treadwell' | 2.7cd |
| 'Elliott' | 2.8bcd |

Means followed by the same letter are not statistically different, P ≤ 0.05, n = 30.

[z] Cluster counts made after the second drop was completed.

TABLE 12

Leaf susceptibility of 'Byrd', 'Huffman', 'Morrill', 'Cunard', 'Tom', 'Treadwell', and 'Sumner' pecans to black pecan aphids at two Georgia locations.

| | Leaf rating [z] | | | |
|---|---|---|---|---|
| | Leary | | Watkinsville | |
| 'Cultivar' | 2009 | 2011 | 2012 | 2011 |
| 'Byrd' | 1.5d | 1.9 | 1.1c | 1.8ab |
| 'Huffman' | 1.4e | 1.4b | 1.1c | 1.0b |

TABLE 12-continued

Leaf susceptibility of 'Byrd', 'Huffman', 'Morrill', 'Cunard', 'Tom', 'Treadwell', and 'Sumner' pecans to black pecan aphids at two Georgia locations.

| | Leaf rating [z] | | | |
|---|---|---|---|---|
| | Leary | | Watkinsville | |
| 'Cultivar' | 2009 | 2011 | 2012 | 2011 |
| 'Morrill' | 2.3b | 1.9a | 2.3a | 2.0a |
| 'Cunard' | 1.1e | 1.9a | 1.3c | 2.0a |
| 'Tom' | 1.1e | 1.2bc | 2.3a | 1.0b |
| 'Treadwell' | 1.9c | 2.1a | 1.2c | 1.8ab |
| 'Sumner' | 2.8a | 1.8a | — | — |

Means followed by the same letter within a column are not statistically different, P ≤ 0.05%, n = 19.

[z] 1 = no injury

2 = <1% of leaves with injury

3 = 1-10% of leaves with injury

4 = 11-50% of leaves with injury

5 = >50% of leaves with injury and partial defoliation.

TABLE 13

Leaf susceptibility of 'Tom', 'Byrd', 'Morrill', 'Huffman', 'Cunard', and 'Treadwell' pecans to pecan leaf scorch mite, Graham Pecan Farm, Leary, Georgia, 2009.

| Cultivar | Leaf rating [z] |
|---|---|
| 'Tom' | 1.1b |
| 'Byrd' | 1.1b |
| 'Morrill' | 1.2b |
| 'Huffman' | 1.6c |
| 'Cunard' | 2.2d |
| 'Treadwell' | 2.7a |

Means followed by the same letter are not statistically different, P ≤ 0.05%, n = 19.

[z] 1 = no damage

2 = trace

3 = multiple lesions

4 = minor defoliation

5 = severe defoliation.

TABLE 14

Leaf scab susceptibility of 'Byrd', 'Morrill', 'Cunard', 'Treadwell', "Tom', 'Elliott', and 'Desirable' pecans at two Georgia locations.

| | Leaf scab [x] | | | | |
|---|---|---|---|---|---|
| | Leary [y] | | | Watkinsville [z] | |
| Cultivar | 2009 | 2010 | 2011 | 2010 | 2011 |
| 'Byrd' | 1.0b | 1.0b | 1.0a | 1.4b | 1.0a |
| 'Morrill' | 1.3b | 1.0b | 1.0a | 2.0b | 1.0a |
| 'Cunard' | 1.3b | 1.b | 1.0a | 1.8b | 1.0a |
| 'Treadwell' | 1.2b | 1.0b | 1.0a | 1.6b | 1.0a |
| 'Tom' | 1.0b | 1.0b | 1.0a | — | 1.0a |
| 'Elliott' | 1.0b | — | — | 1.0a | |
| 'Desirable' | 4.7a | 2.9a | 1.4a | 3.8a | 1.0a |

Means followed by the same letter within a column are not statistically different, P ≤ 0.05.

[x] 1 = no scab lesions

2 = occasional lesion on leaf, less than 1% of leaves with lesions

3 = lesions scant on 2 to 10% of leaves

4 = lesions widespread but no leaf distortion

5 = lesions widespread and severe leaf distortion.

[y] n = 19, trees sprayed with fungicide.

[z] n = 5, trees sprayed with fungicide.

TABLE 15

Fruit scab susceptibility of 'Tom', 'Morrill', 'Cunard', 'Treadwell', 'Byrd', 'Huffman', and 'Desirable' pecans at two Georgia locations.

| Cultivar | Fruit scab [z] Leary [y] 2012 | Watkinsville [z] Five year average |
|---|---|---|
| 'Tom' | 1.0a | 1.0c |
| 'Morrill' | 1.0a | 1.8b |
| 'Cunard' | 1.0a | 2.3b |
| 'Treadwell' | 1.0a | 2.2b |
| 'Byrd' | 1.0a | 1.7bc |
| 'Huffman' | 1.0a | 1.0c |
| 'Desirable' | 4.3b | 3.3a |

Means followed by the same letter within a column are not statistically different, P ≤ 0.05.
[z] 1= no lesions
2 = occasional lesions, <10% of fruit with scab
3 = lesions common on fruit but not damaging, 1-50% of fruit with scab
4 = wide spread lesions on fruit but not damaging, 51-75% of fruit with scab
5 = widespread lesions on fruit, fruit size suppressed, n = 19.
[y] n = 19
[x] Years 2005, 08, 09, 10, 11,12, n = 5, trees sprayed with fungicide.

TABLE 16

Fruit scab susceptibility of 'Tom' and 'Desirable', Leary, Georgia, Aug. 28, 2013.

| Cultivar [y] | Fruit scab rating [z] |
|---|---|
| 'Tom' | 1.0a |
| 'Desirable' | 4.0b |

Means followed by the same letter are not statistically different, P ≤ 0.05.
[z] 1 = no lesions TABLE 16-continued Fruit scab susceptibility of 'Tom' and 'Desirable', Leary, Georgia, Aug. 28, 2013.

| Cultivar [y] | Fruit scab rating [z] |
|---|---|

2 = occasional lesions, <10% of fruit with scab
3 = lesions common on fruit but not damaging, 1-50% of fruit with scab
4 = wide spread lesions on fruit but not damaging, 51-75% of fruit with scab
5 = widespread lesions on fruit, fruit size suppressed.
[y] n = 4, trees sprayed with fungicides.

TABLE 17

Fruit scab susceptibility of 'Tom' and 'Desirable', Albany, Georgia—five year average [y].

| Cultivar | Fruit scab rating [z] |
|---|---|
| 'Tom' | 1.0a |
| 'Desirable' | 3.0b |

Means followed by the same letter are not statistically different, P ≤ 0.05.
[y] years 2009-2013, n = 5, trees sprayed with fungicides.
[z] 1 = no lesions
2 = occasional lesions, <10% of fruit with scab
3 = lesions common on fruit but not damaging, 1-50% of fruit with scab
4 = wide spread lesions on fruit but not damaging, 51-75% of fruit with scab
5 = widespread lesions on fruit, fruit size suppressed.

I claim:

1. A new and distinct cultivar of pecan tree, substantially as herein illustrated and described.

* * * * *